(12) United States Patent
Maikap et al.

(10) Patent No.: US 7,608,730 B2
(45) Date of Patent: Oct. 27, 2009

(54) PROCESS FOR THE PREPARATION OF AN ANTI-TUMOR PLATINUM (II)—COMPLEX

(75) Inventors: Golak Chandra Maikap, Ghaziabad (IN); Bhagat Raj, Ghaziabad (IN); Pradipta Kumar, Ghaziabad (IN); Kannan Vivekanandan, Ghaziabad (IN); Chandrakant Belwal, Ghaziabad (IN)

(73) Assignee: Fresenius Kabi Oncology Limited, New Delhi (IN)

( * ) Notice: Subject to any disclaimer, the term of this patent is extended or adjusted under 35 U.S.C. 154(b) by 0 days.

(21) Appl. No.: 10/588,397

(22) PCT Filed: Feb. 5, 2004

(86) PCT No.: PCT/IN2004/000035

§ 371 (c)(1),
(2), (4) Date: Mar. 26, 2008

(87) PCT Pub. No.: WO2005/075489

PCT Pub. Date: Aug. 18, 2005

(65) Prior Publication Data

US 2008/0207935 A1    Aug. 28, 2008

(51) Int. Cl.
*C07F 15/00*    (2006.01)
(52) U.S. Cl. .................................... 556/137
(58) Field of Classification Search ............... 556/137
See application file for complete search history.

(56) References Cited

U.S. PATENT DOCUMENTS

| 4,169,846 A | 10/1979 | Kidani et al. |
| 5,290,961 A | 3/1994 | Okamoto et al. |
| 5,298,642 A | 3/1994 | Tozawa et al. |
| 5,338,874 A | 8/1994 | Nakanishi et al. |
| 5,420,319 A | 5/1995 | Okamoto et al. |
| 5,585,511 A | 12/1996 | Yokoi et al. |
| 5,939,133 A | 8/1999 | Ganapathi et al. |

FOREIGN PATENT DOCUMENTS

| EP | 0 625 523 | 11/1994 |
| JP | 59-21697 | 2/1984 |
| JP | 60-34982 | 2/1985 |
| JP | 2-212497 | 8/1990 |
| WO | WO 03/004505 | 1/2003 |
| WO | WO 03/106469 | 12/2003 |

*Primary Examiner*—Porfirio Nazario Gonzalez
(74) *Attorney, Agent, or Firm*—Reed Smith LLP; Nanda P. B. A. Kumar

(57) ABSTRACT

We disclose here processes for making Platinum complex of general formula (I) where in, the conformation of 1,2-diaminocyclohexane is cis, trans-l or trans-d isomer and $R_1$ and $R_2$ combinedly make dicarboxylic acid having formulae (II), (III) and (IV), here in, the two carboxylic acid groups are on the same or on vicinal carbon atoms, n is zero or an integer ranging from 1 to 5 and $R_3$ is either hydrogen or a substituent with electron withdrawing or electron releasing effects exemplified by alkoxy, halo, and nitro groups by reacting a compound of formula $M_2PtX_4$ wherein X represents halogen atom such as Cl or Br or thiocyanate with (i) 1,2-diaminocyclohexane (ii) source of silver ion selected from a silver compound containing divalent anion in presence of a corresponding carboxylic acid of formula (II) or (III) or (IV) to get the compound of formula (I), purifying the said compound by treating with alkali metal iodide and isolating the title compound by any conventional methods. The preparation of the said compound involves, for the first time, the intermediate formation of cis-Diiodo-trans-l-1,2-diaminocyclohexane platinum(II) and biscarboylato-trans-l-1,2-diaminocyclohexane platinum(II).

19 Claims, 2 Drawing Sheets

PROCESS FOR THE PREPARATION OF AN ANTI-TUMOR PLATINUM (II)—COMPLEX

FIELD OF THE INVENTION

The present invention relates to a process for the preparation of platinum complex. Particularly, the invention relates to platinum (II) based complex. More particularly, the present invention relates to a process for the preparation of a platinum (II) complex of 1,2-diaminecyclohexane. Even more particularly, the invention relates to a process for the preparation of a platinum (II) complex of general formula I

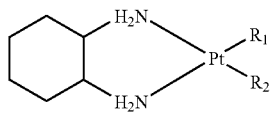

wherein, the conformation of 1,2-diaminocyclohexane is cis, trans-l or trans-d isomer and $R_1$ and $R_2$ combinedly make dicarboxylic acid having formulae II, III and IV,

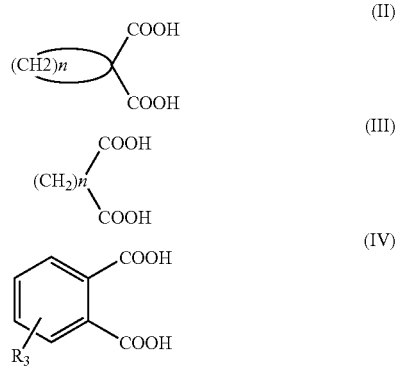

wherein, the two carboxylic acid groups are on the same or on vicinal carbon atoms, n is zero or an integer ranging from 1 to 5 and $R_3$ is either H or a substituent with electron withdrawing or electron releasing effects exemplified by alkoxy, halo and nitro groups. Still more particularly, the present invention relates to a process for the preparation of a platinum (II) complex of 1,2-diaminecyclohexane of formula I as defined above using a source of silver ion selected from a silver compound containing divalent anion. Yet more particularly, the present invention provides a process that is cost effective, high yielding, easy to operate and industrially feasible while maintaining the quality of the title compound. Further, the title compound prepared by the process of the present invention contains reduced impurities (less than 0.1% oxalic acid), conforming to the standards laid down by European pharmacopoeia. Still more particularly, certain alternate optional routes for the main process as disclosed in the present invention results in the formation of intermediates, thereby making the process more advantageous. The platinum (II) complexes prepared by the process described and claimed in this invention are highly active antitumor agents with reduced impurities and thus are useful as active component of carcinostatic drugs.

BACKGROUND OF THE INVENTION

A reference may be made to an unexamined published Japanese patent application No. JP 212497 and examined Japanese patent publication Nos. 66318 and 79353 reporting that a compound in which platinum is coordinated to 1,2-diamino cyclohexane has excellent antitumor effect and relatively high safety. These substances, however, have disadvantages in that their pharmacological effects and safety are not always satisfactory and their administration by injection are limited because of their low solubility in water.

The first report on cis-oxalato-trans-l-1,2-diaminocyclohexane platinum(II) known as oxaliplatin was published in the year 1976 (Y. Kidani et al.). The authors synthesised cis-dichloroplatinum(II) compounds with cis, trans-l and trans-d isomers of 1,2-diaminocyclohexane as ligands and tested against either L-1210 or P-388 in CDF1 mice. The results showed the complex with trans-l ligand highly active. The cis-platin administration causes number of side effects such as renal toxicity, blood toxicity, nervous toxicity and digestive organ toxicity. In order to decrease the toxicity of these complexes, they prepared the mixed ligand complexes with dicarboxylic acids. Since then a no. of patents have appeared for the synthesis of different platinum compounds including oxaliplatin.

Conventionally, the compounds of formula I are prepared by following steps: reacting $K_2PtX_4$ (x is Cl or Br) with a 1,2-cyclohexanediamine isomer to form an intermediate cis-dihalo1,2-diaminocyclohexane wherein, halo could be chloro or bromo; dissolving the intermediate thus obtained in water under boiling; adding thereto a solution of silver nitrate in an amount of twice the mol equivalent of the said intermediate compound; separating the resultant precipitate of silver chloride or bromide through filtration; and adding corresponding dibasic organic acid to the filtrate.

However, the compounds of formula I obtained through the herein above-mentioned process contain dihydroxoplatinum complex as an impurity. Additionally the compounds thus prepared also contain other impurities such as unreacted intermediate, by-products of the said intermediate such as partially reacted chloroaquo, diaquodinitrate and unreacted silver ion thereby reducing the quality of the desired compound. One of the reasons of these impurities is low solubility of the intermediate in water. Further, because of high volume of water used in the reaction to take care of low solubility of the intermediate compound cis-dihalo1,2-diaminocyclohexane, the resulting precipitated silver chloride or bromide goes in to solution making it difficult if not impossible to remove the same completely.

U.S. Pat. No. 5,585,511 describes a platinum complex, which is highly soluble in water and thus can be used for preparing injectable formulations for treating malignant tumour. The compound is prepared as follows: reacting 1,2-diaminecyclohexane platinum(II) complex with silver nitrate in an amount 1.8 to 2 moles per mole of the said platinum complex, then reacting the diaquo complex thus formed with carboxylic acid and alkali, the resulting nitrato compound, where only one nitrate group is replaced, is further treated with halide so as to replace nitrate by halo group. This is extension of conventional method there by getting water soluble value added compound.

The prior art, as known to the inventor additionally includes U.S. Pat. No. 5,290,961. This patent describes a process that obviates the problems posed by the conventional process as mentioned herein above. The process advocates addition of sodium or potassium iodide to the reaction mixture, prior to the addition of organic dibasic acid, to convert the unreacted silver ion and cis-dihalo1,2-diaminocyclohexane into their iodine compounds. On removal of these iodine compounds by simple filtration organic dibasic acid is added to obtain the title compound. The disadvantage is the requirement of large amount of water. Similarly nitrate being monovalent, the amount of silver nitrate required for the reaction will be on higher side.

U.S. Pat. No. 5,939,133 teaches use of deoxygenated water in all steps and substituting nitrogen or an inert gas for air in an operational environment to produce low oxygen content atmosphere. Alternately degassing of an operational environment is proposed to eliminate the possibility of direct oxidation of platinum compound.

This process requires stringent operational conditions thereby making a process cost intensive.

U.S. Pat. Nos. 5,420,319; 5,298,642 and 5,338,874 disclose oxaliplatin with high optical purity through optical resolution. According to the process of these inventions, the starting material is optically resoluted by high performance liquid chromatography (HPLC) to the desired level and then reacted with tetrahalogen platinum (IV) and equimolar silver oxalate followed by reducing to the title compound. Alternately silver oxalate is substituted by silver nitrate or sulfate. Under these conditions the complex thus obtained is further reacted with oxalic acid to produce cis-oxalato(transl-1,2-cyclohexanediamine) Pt(II) complex.

Very recently Debio Pharm S. A. has published a patent (Koji Okamoto et al, WO 03/004505) claiming the invention of oxaliplatin active substance with low oxalic acid content (not more than 0.08%) thereby obtaining a product with reduced toxicity. The process of this invention advocates preparing dichloro(trans-l-1,2-cyclohexanediamine)platinum(II) by reacting $K_2Pt(II)Cl_4$ with trans-l-1,2-cyclohexanediamine, then adding 1.6 equivalents in respect to said compound, silver nitrate, then optionally adding potassium or sodium iodide and adding active carbon under stirring, filtering and treating the filtrate with alkali metal salt of oxalic acid. The crystalline oxaliplatin thus obtained is purified by washing repeatedly with water having pH between 4.5-7.0.

This patent is modification of U.S. Pat. No. 5,290,961. The compound obtained has oxalic acid below detectable limits.

SUMMARY OF THE INVENTION

In consequence, it therefore becomes an object of the present invention to provide a process to prepare a platinum complex having excellent anti-tumor activity, equivalent safety and substantially free from impurities such as un-reacted intermediate i.e. platinum complex of 1,2-diaminocylohexane, by-products of the said intermediate like partially reacted chloroaquo, diaquodinitrate, oxalic acid (less than 0.1%) and un-reacted silver ion.

Other object of this invention is to provide a process for the preparation of a platinum (II) based compound, which can be employed as an active ingredient for preparing formulations having carcinostatic effects.

Another object of this invention is to provide a process for the preparation of a platinum (II) complex of 1,2-diaminecyclohexane obviating the various drawbacks of the existing processes as described herein above.

Yet another object of this invention is to provide a process for the preparation of platinum (II) complex of general formula I as defined above.

Still another object of this invention is to provide a process for the preparation of a platinum (II) complex of 1,2-diaminecyclohexane of formula I as defined above using a source of silver ion selected from a silver compound containing divalent anion.

Yet another object of this invention is to provide a process that is cost effective, high yielding, efficient, easy to operate, do not require any stringent operational conditions or sophisticated infrastructure and industrially feasible while maintaining the quality of the title compound.

Still another object of this invention is to provide a process with certain alternate optional routes that involves formation of intermediates such as cis-diiodo-trans-l-1,2-diamino cyclohexane platinum (II) and cis-biscarboxylato-trans-l-1,2-diaminocyclohexane platinum (II) thereby making the process more advantageous.

After continuous experimentation, it was observed that in the hitherto known processes, during the reaction between cis-dihalo 1,2-diaminocyclohexane and source of silver ion, when silver nitrate or sulfate are used as a source of silver ion, sulfate ions and nitrate ions react with the alkali metals present in dibasic organic acid resulting into nitrates or sulfates of alkali metal. During recovery of the title compound by removal of water, these salts remain in the title compound as an impurity. However, this problem is taken care of by using selective silver salt as a source of silver ion, in the process of the present invention.

Accordingly the present invention provides a process for the preparation of the preparation of a platinum complex of general formula I

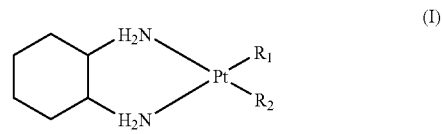

Where in, the conformation of 1,2-diaminocyclohexane is cis, trans-l or trans-d isomer and $R_1$ and $R_2$ combinedly make dicarboxylic acid having formulae II, III and IV,

where in, the two carboxylic acid groups are on the same or on vicinal carbon atoms, n is zero or an integer ranging from 1 to 5 and $R_3$ is either hydrogen or a substituent with electron withdrawing or electron releasing effects exemplified by alkoxy, halo, and nitro groups which comprises, reacting a compound of formula $M_2PtX_4$ wherein X represents halogen atom such as Cl or Br or thiocyanate with (i) 1,2-diaminocyclohexane (ii) source of silver ion selected from a silver compound containing divalent anion in presence of a corresponding dicarboxylic acid of formula II or III or IV to get the compound of formula I, purifying the said compound by treating with alkali metal iodide and isolating the title compound by any conventional methods.

In an embodiment of this invention, in a process for the preparation of Platinum complex of a compound of formula I as defined herein above (i) a compound having formula V obtained through a reaction of a compound $M_2PtX_4$, where X has the meaning as given above with 1,2-diaminocyclohexane in water is added to a solution of silver ion and dicarboxylic acid of formula II or III or IV (ii) the reaction mixture is filtered out on completion of the reaction, (iii) the filtrate thus obtained is reacted with alkali metal iodide, followed by filtering and isolating the title compound from the filtrate by any known methods.

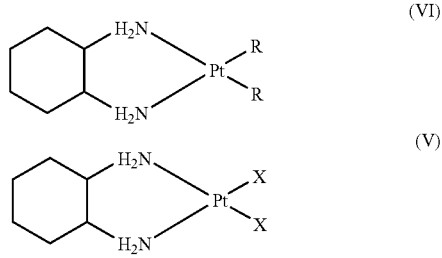

In other embodiment of this invention, in a process for the preparation of Platinum complex of a compound of formula I as defined herein above, (i) a compound having formula V obtained through a reaction of a compound $M_2PtX_4$, where X has the meaning as given above with 1,2-diaminocyclohexane in water is added to a solution of silver ion and corresponding carboxylic acid to get bis carboxylato-trans-l-1,2-diamino cyclo hexane platinum (II) of formula VI, wherein, R can be aliphatic carboxylic acid either straight chain or branched or sulphonic acid, saturated or unsaturated with 1 to 5 carbon atoms, or alicyclic monocarboxylic acid of formula VII,

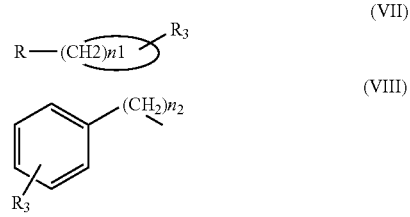

wherein, $n_1$, is an integer ranging from 2 to 8 and $R_3$ has the same meaning as defined above or an aromatic carboxylic or sulphonic acid of formula VIII wherein, $n_2$ is in the range of 1 to 3 carbon atoms, saturated or unsaturated and $R_3$ has the same meaning as given above, (ii) the reaction mixture is filtered out on completion of the reaction, the filtrate thus obtained is reacted with alkali metal salt of corresponding dicarboxylic acid followed by isolating the title compound by any conventional methods.

In still other embodiment of this invention, in a process for the preparation of Platinum complex of a compound of formula I as defined above, (i) 1,2-diaminocyclohexane in water is added to alkali metal tetraiodoplatinate obtained through reaction of a compound $M_2PtX_4$, where X has the same meaning as given above with alkali metal iodide to obtain an intermediate, cis-diiodo1,2-diaminocyclohexaneplatinum (II) of formula V (X=I), the said iodo compound is reacted with a solution of silver ion and corresponding dicarboxylic acid of formula II or III or IV followed by isolating the title compound, which is also represented by oxaliplatin, by any conventional methods.

In another embodiment of this invention, in a process for the preparation of Platinum complex of a compound of formula I as defined above, (i) 1,2-diaminocyclohexane in water is added to alkali metal tetraiodoplatinate obtained through reaction of a compound $M_2PtX_4$, where X has the same meaning as given above with alkali metal iodide to obtain an intermediate, cis-diiodo-1,2-diaminocyclohexaneplatinum (II) of formula V (X=I), (ii) the said iodo compound is reacted with a solution of silver ion and corresponding carboxylic acid of formula VII or VIII to get bis carboxylato-trans-l-1,2-diaminocyclohexaneplatinum (II) of formula VI, which has been defined above (iii)) the reaction mixture is filtered out on completion of the reaction, the filtrate thus obtained is reacted with alkali metal salt of corresponding dicarboxylic acid followed by isolating the title compound by any conventional methods.

In still another embodiment of this invention, in the $M_2PtX_4$, M may represent sodium or potassium preferably potassium and X may represent Cl or Br or thiocyanate preferably Cl or Br more preferably Cl.

In yet another embodiment of this invention, source of silver ion selected from a silver compound containing divalent anion, the divalent anion may represent carbonate or oxide, preferably oxide.

In a further embodiment of this invention the carboxylic acid employed may be selected from aliphatic carboxylic acids straight chain or with branching, preferably straight chain aliphatic carboxylic acid, more preferably straight chain aliphatic carboxylic acid with 1-3 carbon atoms, even more preferably acetic acid.

The sulphonic acid employed may be selected from aliphatic sulphonic acids straight chain or with branching, preferably straight chain aliphatic sulphonic acid, more preferably straight chain aliphatic sulphonic acid with 1-3 carbon atoms, even more preferably methanesulphonic acid.

The alkali metal iodide used may be sodium or potassium iodide.

The alkali metal salt of dicarboxylic acid employed may be selected from aliphatic, alicyclic or aromatic dicarboxylic acid, preferably from aliphatic, more preferably from aliphatic with 2 to 5 carbon atoms, even more preferably from aliphatic with 2 carbon atoms.

The ratio of (a) $M_2PtX_4$ to 1,2-diaminocyclohexane may ranges from 1 to 1.2, preferably 1 to 1; (b) source of silver ion to platinum (II) complex of formula V ranges from 1 to 2.2, preferably 1 to 2; (c) carboxylic acid to silver ion varies from 1 to 1.2; (d) alkali metal salts of dicarboxylic acid to bis carboxylato-1,2-diaminocyclohexaneplatinum (II) of formula VI, ranges between 0.7 to 1.2 and (e) diiodo compound of formula V (X=I), to silver ion in carboxylic acid ranges from 1 to 1.

The reaction between (a) $M_2PtX_4$ & 1,2-diaminocyclohexane may be conducted at a temperature of 15 to 40° C., preferably 25 to 30° C.; (b) of source of silver ion and cis-platinum (II) complex of formula V is performed at 40 to 80° C., preferably 60 to 70° C.; (c) between alkali metal salts of dicarboxylic acid and bis carboxylato-1,2-diaminocyclohexaneplatinum (II) of formula VI, is effected at a temperature in the range of 50 and 60° C. and (d) that in between diiodo compound of formula V and silver ion in presence of carboxylic acid is carried out at 60 to 70° C. and the reactions are monitored with chromatography.

The reaction (a) as intended to be claimed, (b) between $M_2PtX_4$ & 1,2-diaminocyclohexane (c) between a source of silver ion and cis-platinum (II) complex of formula V (d)

between alkali metal salts of dicarboxylic acid and bis carboxylato-1,2-diaminocyclohexaneplatinum (II) of formula VI, and (e) that in between diiodo compound of formula V and silver ion in presence of carboxylic acid may be effected at least for a period of two hours, preferably for 5 to 10 hours, more preferably for 5 to 7 hours.

The isolation of the title compound may be effected by filtration, centrifugation, evaporation followed by drying so as to get a product with loss on drying (LOD) not exceeding 0.5% and the drying may be carried out at a temperature less than 100° C. preferably under vacuum.

The platinum (II) complex prepared by the process of the present invention also includes the hydrates and solvates of the product.

Further, the process, with which the current invention is concerned, is described below by schemes and text.

Though the schemes are illustrated mainly by oxaliplatin, a representative of compound of formula I, the process of this invention is not intended to restrict to oxaliplatin. The schemes can equally be used for all other compounds of general formula I using corresponding variable reactants.

SCHEMES

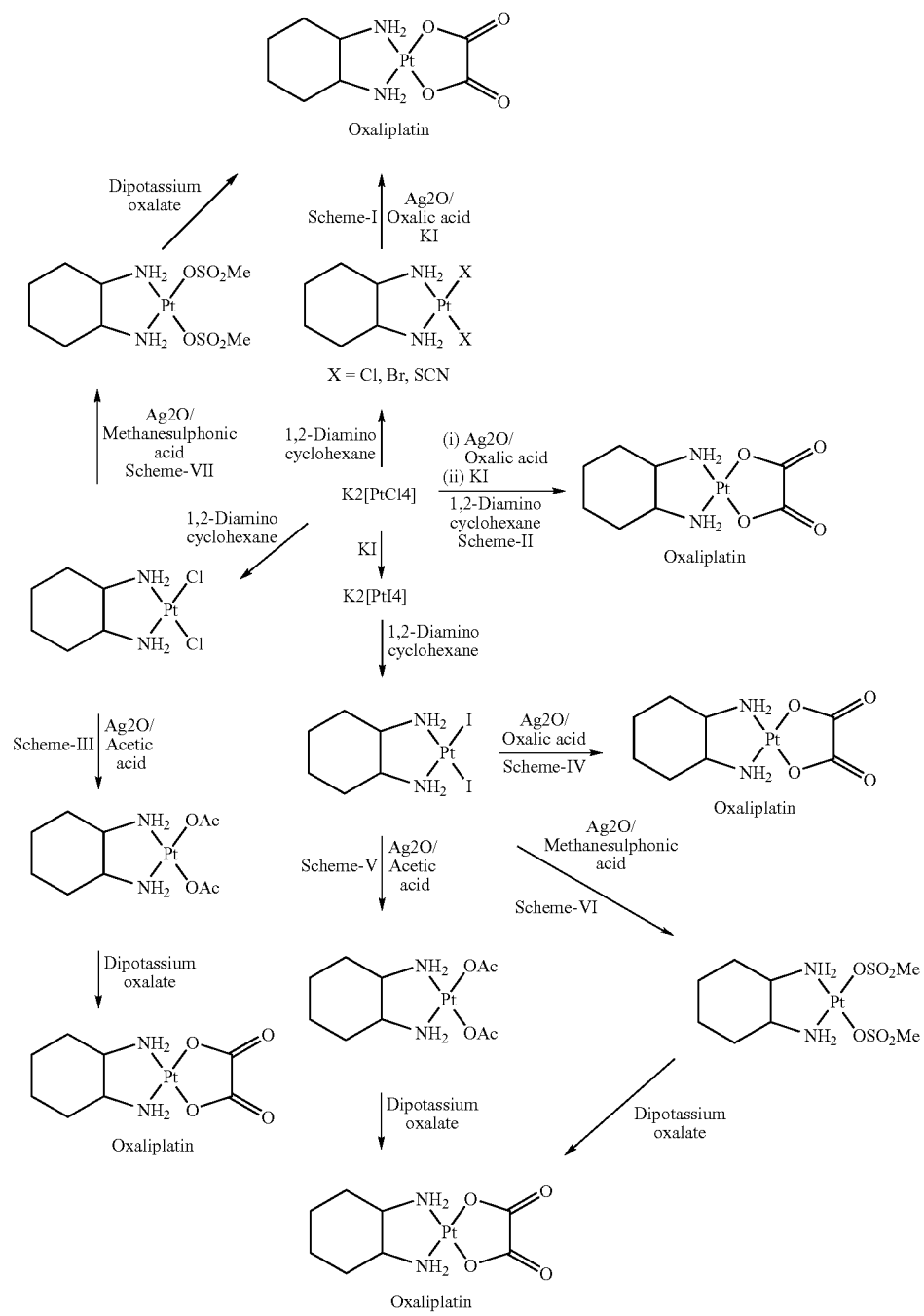

Potassium tetrachloroplatinate is first converted to potassium tetraiodoplatinate by treatment with potassium iodide in water and subsequent addition of trans-l-1,2-diaminocyclohexane to the above solution in 1:1 molar ratio at ambient temperature produces cis-diiodo-trans-l-1,2-diaminocyclohexane platinum(II) as a yellow coloured solid. This is filtered, dried and subsequently used in the different synthetic schemes.

Cis-dichloro-trans-l-1,2-diaminocyclohexane platinum (II) (Structure-V, X=Cl) is prepared (Example-2) by the method described in U.S. Pat. No. 5,290,961. The cis-bis carboxylato-trans-l-1,2-diaminocyclohexane platinum(II) of formula VI is prepared from the corresponding dihalo compound by treatment with the carboxylic acid in presence of silver ion. Cis-bissulphonato-trans-l-1,2-diaminocyclohexane platinum(II) is prepared from the dihalo compound by treatment with sulphonic acid and a source of silver ion. These intermediates are subsequently converted to dicarboxylate platinum compounds by treatment with salts of dicarboxylic acids.

Scheme-I

Potassium tetrachloroplatinate is converted to cis-dichloro-trans-l-1,2-diaminocyclohexane platinum(II). This is further converted to oxaliplatin and related compounds by reacting with dicarboxylic acid and silver oxide in water. The silver salts are filtered off and the filtrate treated with potassium iodide to remove silver ions as silver iodide. Water recovery followed by decolourisation with active carbon produces oxaliplatin.

Scheme-II

This is a one-pot reaction involving all the reagents together. Cis-dihalo-trans-l-1,2-diaminocyclohexane platinum(II) is formed in-situ which is converted to Platinum compounds (Structure-I) by reaction with the dicarboxylic acids and silver oxide present.

Scheme-III

We report here the formation of diacetato as an intermediate which dissolves in the reaction medium. The silver chloride formed is filtered repeatedly till we get a clear filtrate. Dipotassium oxalate is added to convert it to oxaliplatin.

Chelation is attributed to be the driving force for the conversion of diacetato to dicarboxylate which is energetically favoured. The intermediate formation of the diacetato has been proved by removing an aliquot, evaporating water and recording the mass spectrum.

The solid diacetato obtained was independently converted to oxaliplatin under the same experimental conditions.

Scheme-IV

The diiodo compound produced as herein above described and supported by Example-1, as herein after illustrated, is converted to oxaliplatin as described in scheme-II.

Scheme-V

The diiodo compound produced as herein after illustrated by Example-1, is converted to the diacetato compound by treatment with acetic acid and silver oxide as in scheme-III. The diacetato in solution, after removal of precipitated silver iodide is treated with dipotassium oxalate to give oxaliplatin.

The less solubility of diiodo intermediate has been taken care of by converting it in to the diacetato and the filtration of silver iodide here does not give any trouble as in case of silver chloride. Silver iodide being highly insoluble, further treatment with sodium or potassium iodide is not required.

Scheme-VI

The diiodide compound produced as herein after illustrated by Example-1 is converted to the disulphonato compound by treatment with silver oxide and methane sulphonic acid. The disulphonato compound in solution, after removal of precipitated silver iodide is treated with dipotassium oxalate to give oxaliplatin (Example-9).

Scheme-VII

Cis-dichloro-trans-l-1,2-diaminocyclohexane platinum (II) produced as herein after illustrated by Example-2 is treated with silver oxide and methanesulphonic acid. The precipitated silver chloride is filtered off and the clear filtrate treated with dipotassium oxalate to produce oxaliplatin (Example-10).

The clear filtrate obtained in example-9 was subjected to mass spectrophotometry. Mass Spectral analysis of cis-dimethanesulphonato-trans-l-1,2-diaminocyclohexane platinum(II) (FIG. 1) showed a mixture peaks corresponding to disulphonato (M+=500), Monosulphonato monoaquo (M+=422), diaquo derivative (M+=344) and sodiated, H2O adducts along with some transient species. Each m/z group was comprised of several mass values corresponding to the major platinum isotopes 194Pt, 195Pt, 196Pt and 198Pt. Proposed structures for observed molecular weights given in Table 1. The pathway for the formation of oxaliplatin is shown in scheme-VIII.

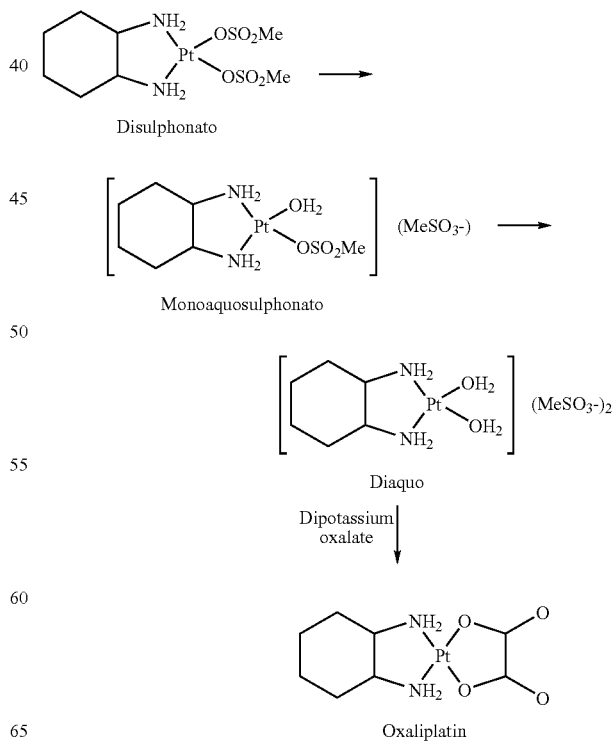

SCHEME-VIII

TABLE 1

| S. No. | Observed Mol. Wt | Mol. Formula | Proposed structure |
|---|---|---|---|
| 1 | 500.0 | C8H20O6N2PtS2 | (1,2-diaminocyclohexane)Pt with bidentate bis(methanesulfonate) |
| 2 | 518 | C8H22O7N2PtS2 | 500 + H2O |
| 3 | 445 | C7H19O4N2PtSNa | (1,2-diaminocyclohexane)Pt(OH2Na)(O-SO2-CH3) |
| 4 | 422 | C7H19O4N2PtS | (1,2-diaminocyclohexane)Pt(OH2)(O-SO2-CH3) |
| 5 | 404 | C7H17O3N2PtS | [(1,2-diaminocyclohexane)Pt(O-SO2-CH3)] |
| 6 | 367 | C6H18O2N2PtNa | (1,2-diaminocyclohexane)Pt(OH2)(OH2) Na |
| 7 | 344 | C6H18O2N2Pt | (1,2-diaminocyclohexane)Pt(OH2)(OH2) |

The intermediates of formulae V (X=I) and VI are integral in the preparation of the title compound hence, they will be claimed as a part of this invention.

The following non-limiting examples are illustrative of the process of the present invention. Any modification, which is obvious to a person skilled in the art and working in this field, may fall within the scope of the present invention. Further, although a process of preparing oxaliplatin as a representative of Platinum (II) based complex of formula I will be illustrated, the examples do not intend to restrict the present invention to oxaliplatin.

EXPERIMENTAL

Figure 1A:
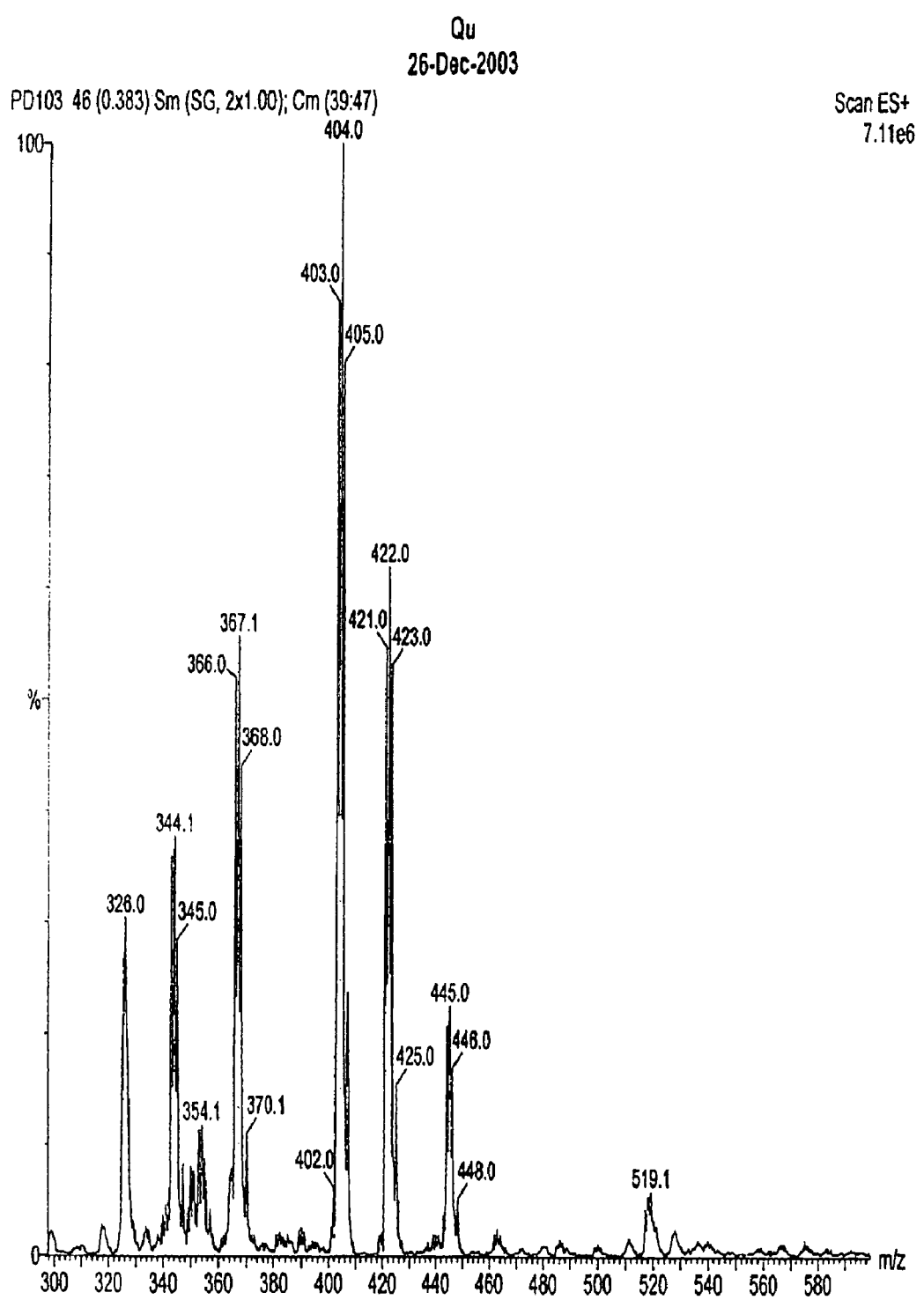
FIG. 1A represents mass spectrum of cis-dimethanesulphonato-trans 1- 1,2-diaminocyclohexane platinum(II), as obtained in Example-9, of the present invention.
Figure 1B:
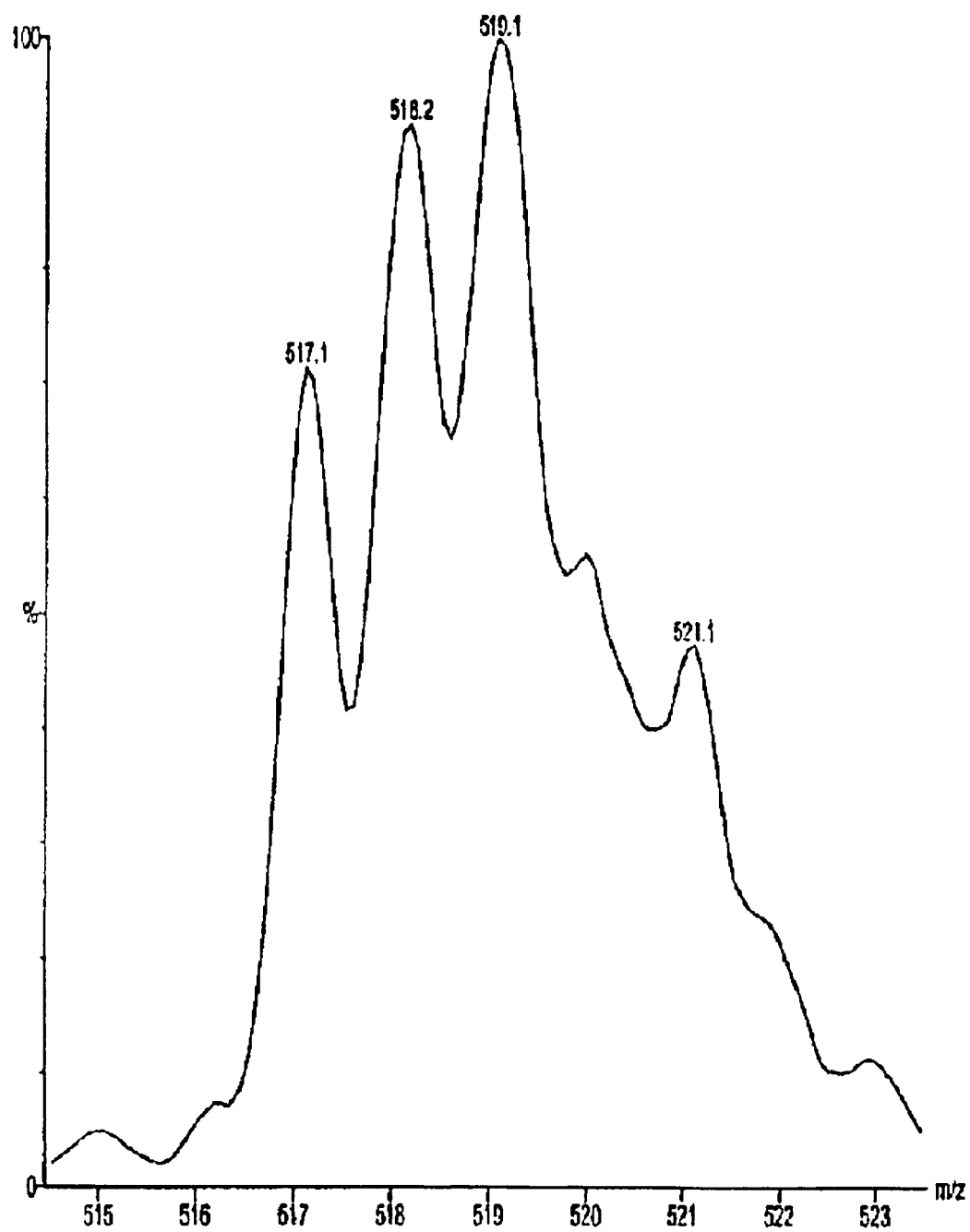
FIG. 1B represents an expansion of specific peaks of mass spectrum (m/z 515-523) of cis-dimethanesulphonato-trans-l-1, 2-diaminocyclohexane platinum (II), as obtained in Example-9, of the present invention.

HPLC analyses were performed on a Shimadzu HPLC with isocratic mobile phase of flow 1 ml/min equipped with a C-18 column, 5μ, 4.6×250 mm and UV-Vis detector at 220 nm. The mobile phase in case of conversion of cis-dichloro-trans-l-1,2-diamino cyclohexane platinum(II) to oxaliplatin was pure buffer containing 0.134% of disodium hydrogen orthophosphate and 0.069% of sodium dihydrogen orthophosphate (System-A). The mobile phase in case of conversion of cis-diiodo-trans-l-1,2-diaminocyclohexane Platinum (II) to cis-diacetato-trans-l-1,2-diaminocyclohexane platinum(II) consists of 15% acetonitrile and 85% buffer containing 0.175% of tetra-n-butyl ammonium hydrogen sulphate (system-B). The mobile phase for the conversion of diacetato to oxaliplatin is carried out using system-A. Mass spectra were recorded using Trans-l-1,2-diaminocyclohexane was procured from Acros Organics and was used as such without further purification.

EXAMPLE-I

Cis-diiodo-trans-l-1,2-diaminocyclohexane platinum(II)

40 g of Potassium iodide (0.24 mol) was added to a clear solution of 25 g of Potassium tetrachloroplatinate (0.06 mol) in 1.5 liters of DM water at 30° C. The colour of the solution changed from cherry red to black. The reaction mixture was stirred for further 30 min. and then 6.87 g of trans-l-1,2-diaminocyclohexane (0.06 mol) was added to the above solution and stirring continued at 30° C. Separation of a yellow solid indicated the formation of cis-diiodo-trans-l-1,2-diaminocyclohexane platinum(II). The reaction was continued for 4-5 h to ensure the complete consumption of potassium tetraiodo platinate (by HPLC).

The solution was filtered and the solid washed with DM water till the filtrate is colourless. The solid was dried at 50° C. (Yield: 30 g, 90%).

EXAMPLE-2

Cis-dichloro-trans-l-1,2-diaminocyclohexane platinum(II)

562.5 g of potassium chloroplatinate and 154.8 g of trans-l-1,2-cyclohexanediamine were dissolved and mixed in 3.5 liters of water to obtain cake-like cis-dichloro(trans-l-1,2-cyclohexanediamine) platinum(II) without recrystallization with a yield of 96%.

EXAMPLE-3

Cis-oxalato-trans-l-1,2-diaminocyclohexane platinum(II) (Oxaliplatin)

A mixture of 50 g of potassium tetrachloroplatinate (0.12 mol), trans-l-1,2-diamino cyclohexane, 13.74 g (0.12 mol), 25.15 g of silver oxide (0.10 mol) and 13.66 g of oxalic acid dihydrate (0.10 mol) were heated together in 3 liters of DM water at 90-100° C. for 10-12 h. The reaction mixture was cooled to 50° C. filtered through celite. The filtrate was treated with 0.5 g of potassium iodide at 30° C. for 10-12 h in dark. Then again filtered through celite. The filtrate was treated with activated carbon to remove colour. Removal of ~2.8 liters of water at 60° C. under vacuum produces oxaliplatin as a white crystalline solid (10 g, 20%).

EXAMPLE-4

Cis-oxalato-trans-l-1,2-diaminocyclohexane platinum(II) (Oxaliplatin)

A mixture of silver oxide (27.14 g, 0.11 mol) and oxalic acid dihydrate (14.75 g, 0.11 mol) and cis-dichloro-trans-l-1,2-diaminocyclohexane platinum(II), 50 g (0.13 mol) prepared as per example-2 in 2.5 liters of DM water was heated at 90-100° C. for 1-2 hours. Temperature of the reaction mixture was brought down to 60° C. The reaction was continued for 12 h at this temperature. Completion of the reaction was checked by HPLC. The reaction mixture was filtered through celite and the filtrate treated with 0.5 g of potassium iodide as in example-3. Carbon treatment followed by water removal produces oxaliplatin (20 g, 38%).

EXAMPLE-5

Cis-oxalato-trans-l-1,2-diaminocyclohexane platinum(II) (Oxaliplatin)

A mixture of 25 g of cis-dichloro-trans-l-1,2-diaminocyclohexane platinum(II) (0.065 mol), 15.25 g of silver oxide (0.065 mol) and acetic acid (7.9 g, 0.13 mol) was heated at 60-70° C. in 1.25 liters of DM water and progress of the reaction monitored by HPLC.

Cis-dichloro compound was consumed in 4-5 h and the cis-diacetato compound was formed in 85-90% (by HPLC). To the reaction was added dipotassium oxalate mono-hydrate (10.76 g, 0.058 mol) and heating continued with reaction monitoring. The reaction was complete in 6 h. The reaction mixture was cooled to RT and filtered through celite 2-3 times to get a clear filtrate which was treated with potassium iodide to remove dissolved silver ions. Carbon treatment and water recovery produces 17.5 g of oxaliplatin (67%).

EXAMPLE-6

Cis-oxalato-trans-l-1,2-diaminocyclohexane platinum(II) (Oxaliplatin)

A mixture of 25 g of cis-dichloro-trans-l-1,2-diaminocyclohexane platinum(II) (0.065 mol), 15.25 g of silver oxide (0.065 mol) and acetic acid (7.9 g, 0.13 mol) was heated at 60-70° C. in 1.25 liters of DM water and progress of the reaction monitored by HPLC.

Cis-dichloro compound was consumed in 4-5 h and the cis-diacetato compound was formed in 85-95% (by HPLC). The reaction mixture was filtered through celite 2-3 times to get a clear filtrate. Water was recovered at 50° C. under reduced pressure to give cis-diacetato-trans-l-diaminocyclohexane platinum(II) as a white solid (21 g, 83%). The above solid (21 g, 0.049 mol) was again dissolved in water 2.1 liters and heated with dipotassium oxalate monohydrate, 8.11 g (0.044 mol) at 60-70° C. for 5-6 h. Workup of the reaction as in example-5 produced 17.5 g of oxaliplatin (67%).

EXAMPLE-7

Cis-oxalato-trans-l-1,2-diaminocyclohexane platinum(II) (Oxaliplatin)

Cis-diiodo-trans-l-1,2-diaminocyclohexane (40 g, 0.07 mol) prepared as per example-1 was heated at 90-100° C. in 2 liters of DM water with 16.48 g of silver oxide (0.07 mol) and oxalic acid dihydrate, 8.06 g (0.06 mol) for 10-12 h. The reaction mixture was filtered through celite and worked up as usual to give 8.3 g of oxaliplatin (30%).

EXAMPLE-8

Cis-oxalato-trans-l-1,2-diaminocyclohexane platinum(II) (Oxaliplatin)

Cis-diiodo-trans-l-1,2-diaminocyclohexane (50 g, 0.09 mol) prepared as per example-1 was heated with stirring in 2.5 liters of DM water at 80-90° C. with acetic acid (10.66 g) and silver oxide, 20.88 g (0.09 mol). The reaction was complete in 4 h (by HPLC). The reaction mixture was filtered through celite and the clear filtrate was treated with dipotassium oxalate monohydrate, 14.9 g (0.08 mmol) at 60° C. under stirring.

The reaction was continued at this temperature for 5 h and then subsequent work up produced 21.44 g of oxaliplatin (60%).

EXAMPLE-9

Cis-bismethanesulphonato-trans-l-1,2-diaminocyclohexane platinum(II)

A mixture of 25 g of cis-dichloro-trans-l-1,2-diaminocyclohexane platinum(II) (0.065 mol), 15.25 g of silver oxide (0.065 mol) and methanesulphonic acid (12.63 g, 0.13 mol) was heated at 60-70° C. in 1.25 liters of DM water and progress of the reaction monitored by HPLC. After the reaction was complete, the mixture was cooled to RT and filtered repeatedly through celite to get a clear filtrate

EXAMPLE-10

Cis-oxalato-trans-l-1,2-diaminocyclohexane platinum(II) (Oxaliplatin)

A mixture of 25 g of cis-dichloro-trans-l-1,2-diaminocyclohexane platinum(II) (0.065 mol), 15.25 g of silver oxide (0.065 mol) and methanesulphonic acid (12.63 g, 0.13 mol) was heated at 60-70° C. in 1.25 liters of DM water and progress of the reaction monitored by HPLC.

Cis-dichloro compound was consumed in 5-6 h and the cis-disulphonato compound was formed in 85-90% (by HPLC). The reaction was filtered through celite to get a clear solution to which was added dipotassium oxalate monohydrate (10.89 g, 0.06 mole) and heating continued with reaction monitoring. The reaction was complete in 6 h.

The reaction mixture was cooled to RT and filtered through celite 2-3 times to get a clear filtrate which was treated with potassium iodide to remove dissolved silver ions. Carbon treatment and water recovery produces 18.2 g of oxaliplatin (70%).

EXAMPLE-11

Cis-oxalato-trans-l-1,2-diaminocyclohexane platinum(II) (Oxaliplatin)

A mixture of 37.14 g of cis-diiodo-trans-l-1,2-diaminocyclohexane platinum(II) (0.065 mol), 15.25 g of silver oxide (0.065 mol) and methanesulphonic acid (12.63 g, 0.13 mol) was heated at 60-70° C. in 1.25 liters of DM water and progress of the reaction monitored by HPLC.

Cis-diiodo compound was consumed in 8-10 h and the cis-disulphonato compound was formed in 75-80% (by HPLC). The reaction mixture was filtered and to the clear filtrate was added dipotassium oxalate monohydrate (10.89, 0.06 mole) and heating continued with reaction monitoring. The reaction was complete in 6 h.

The reaction mixture was cooled to RT and filtered through celite 2-3 times to get a clear filtrate. Carbon treatment and water recovery produces 15.6 g of oxaliplatin (60%).

ADVANTAGES

The process is economical.
The process is industrially feasible.
The process is user friendly.
The process is high yielding.
The product obtained by the process of the present invention has better quality with respect to impurities. The title product has reduced impurities conforming to the standards laid down by European pharmacopoeia.

We claim:

1. A process for the preparation of a platinum (II) complex compound of general formula (I)

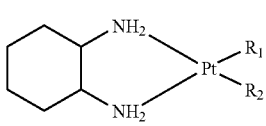

(I)

wherein the conformation of 1,2-diaminocyclohexane is cis, trans-(l) or trans-(d) isomer and $R_1$ and $R_2$ combinedly make dicarboxylic acid anion having formulae II, III and IV

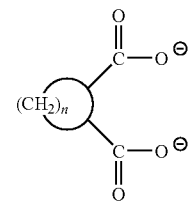

(II)

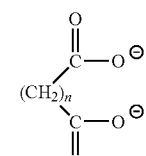

(III)

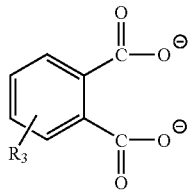

(IV)

wherein n is zero or an integer ranging from 1 to 5 and $R_3$ is H, alkoxy, halo or a nitro group comprising the steps of:

i) reacting a compound of formula $M_2PtX_4$ wherein X represents thiocyanate or a halogen atom selected from Cl, Br, and I with 1,2-diaminocyclohexane to give a compound of formula (V);

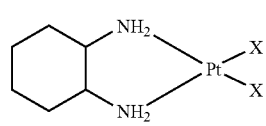

(V)

ii) reacting the compound of formula (V) of step i), with a source of silver ion selected from a silver compound containing divalent anion in presence of an aliphatic carboxylic acid or an aliphatic or aromatic sulphonic acid to give compound of formula (VI)

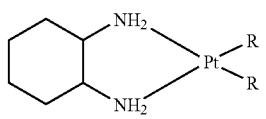

(VI)

wherein R is —O—CO—R' or O—SO$_2$—R', wherein R' is H, an alkyl or an aryl group; and iii) reacting the compound of formula (VI) of step ii), with a dicarboxylic acid or its salts to give the object platinum (II) complex compound of formula (I).

2. A process according to claim 1, wherein the conformation of 1,2-diaminocyclohexane is trans-(l).

3. A process according to claim 1, wherein the Platinum (II) complex compound is cis-oxalato-trans-(l)-1,2 diamino cyclohexane Platinum.

4. A process according to claim 1, wherein in the compound of formula $M_2PtX_4$, M represents sodium or potassium and X represents Cl, Br, I or thiocyanate.

5. A process according to claim 4, wherein the compound of formula $M_2PtX_4$ is Potassium tetrachloroplatinate.

6. A process according to claim 1, wherein the source of silver ion is silver carbonate or silver oxide.

7. A process according to claim 1, wherein the source of silver ion is silver oxide.

8. A process according to claim 1, wherein the aliphatic carboxylic acid is straight chained or branched having 1 to 5 carbon atoms.

9. A process according to claim 1, wherein the aliphatic carboxylic acid is acetic acid.

10. A process according to claim 1, wherein the aliphatic sulphonic acid is straight chained or branched having 1 to 5 carbon atoms.

11. A process according to claim 7, wherein the aliphatic sulphonic acid is methanesulphonic acid.

12. A process according to claim 1, wherein the dicarboxylic acid salt is dipotassium oxalate.

13. A process according to claim 1, wherein the mole ratio of $M_2PtX_4$ to 1,2-diaminocyclohexane is between 1.0 and 1.2.

14. A process according to claim 1, wherein step i) is carried out at a temperature of between 15° C. and 40° C.

15. A process according to claim 1, wherein the mole ratio of the source of silver ion to the compound of formula (V) is between 1.0 and 2.2.

16. A process according to claim 1, wherein the step ii) is carried out at a temperature of between 40° C. and 80° C.

17. A process according to claim 1, wherein the mole ratio of the source of silver ion to the aliphatic carboxylic acid or the aliphatic/aromatic sulphonic acid is between 1.0 and 1.2.

18. A process according to claim 1, wherein the mole ratio of compound of formula (VI) to the dicarboxylic acid or its salts is between 0.7 and 1.2.

19. A process according to claim 1, wherein the step iii) is carried out at a temperature of between 50° C. and 75° C.

* * * * *